(12) United States Patent
Cerletti

(10) Patent No.: US 7,057,016 B2
(45) Date of Patent: *Jun. 6, 2006

(54) PROCESS FOR THE PRODUCTION OF BIOLOGICALLY ACTIVE PROTEIN

(75) Inventor: Nico Cerletti, Bottmingen (CH)

(73) Assignee: Novartis Corporation, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/813,271

(22) Filed: Mar. 20, 2001

(65) Prior Publication Data

US 2002/0115834 A1    Aug. 22, 2002

Related U.S. Application Data

(63) Continuation of application No. 09/316,724, filed on May 21, 1999, now abandoned, which is a continuation of application No. 08/776,444, filed on Jan. 24, 1997, now abandoned.

(30) Foreign Application Priority Data

Jul. 25, 1994    (EP)    .................. 94810439

(51) Int. Cl.
- C07K 14/495    (2006.01)
- C07K 5/08    (2006.01)
- C08K 5/41    (2006.01)
- C08K 5/16    (2006.01)

(52) U.S. Cl. ...................... 530/350; 530/408; 530/409; 530/410; 524/173; 524/233

(58) Field of Classification Search ................ 530/350; 524/173, 233; 554/109
See application file for complete search history.

(56) References Cited

U.S. PATENT DOCUMENTS

| | | | |
|---|---|---|---|
| 4,455,381 A * | 6/1984 | Magnusson et al. | 436/543 |
| 4,572,798 A | 2/1986 | Koths et al. | 260/112 |
| 4,620,948 A | 11/1986 | Builder et al. | 530/419 |
| 4,731,440 A | 3/1988 | Bentle et al. | 530/399 |
| 4,742,003 A | 5/1988 | Derynck et al. | 435/68 |
| 5,144,006 A | 9/1992 | Tam | 530/345 |
| 5,162,507 A | 11/1992 | Wolfe et al. | 530/412 |
| 5,407,810 A * | 4/1995 | Builder et al. | 435/69.1 |
| 5,453,363 A | 9/1995 | Rudolph et al. | 435/69.1 |
| 5,843,463 A * | 12/1998 | Krivan et al. | 424/256.1 |
| 6,057,430 A * | 5/2000 | Cerletti | 530/402 |

FOREIGN PATENT DOCUMENTS

| EP | 0114506 | 1/1984 |
|---|---|---|
| EP | 200341 | 11/1986 |
| EP | 0208539 | 1/1987 |
| EP | 0267463 | 5/1988 |
| EP | 0268561 | 5/1988 |
| EP | 0277313 | 8/1988 |
| EP | 0293785 | 12/1988 |
| EP | 0302469 | 2/1989 |
| EP | 0433225 | 6/1991 |
| EP | 0542679 | 5/1993 |
| WO | 8605809 | 10/1986 |
| WO | 88/05788 | 8/1988 |
| WO | 8808003 | 10/1988 |
| WO | 8808849 | 11/1988 |
| WO | 9014359 | 11/1990 |
| WO | WO 9603432 A1 * | 2/1996 |

OTHER PUBLICATIONS

Rudolph, R. "Renaturation of recombinant, disulfide-bonded proteins from inclusion bodies." In, Modern Methods in Protein and Nucleic Acid Research; Tschesche, H., Ed.; Walter de Grutyer: Berlin, New York, Jan. 1991; pp. 149-171.*
Tam, et al., J. Am. Chem. Soc. vol. 113, 1991, pp. 6657-6662.
Tam, et al., Int. J. Peptide Protein Res., vol. 39, 1992, pp. 464-471.
Akaji, et al., Peptide Chemistry, 1991; A. Zuzuki (ed.) Protein Res.; Foundation Oska 1992, pp. 125-128.
Otaka, et al., Tetrahedron Letters, vol. 32, No. 9, 1991, pp. 1223-1226.
Akaji, et al., J. Am. Chem. Soc. 1992, vol. 114, pp. 4137-4143.
Wozney, et al., Science vol. 242, 1988, pp. 1528-1534.
Takuwa, et al., Bioch, Biophys. Res. Commun. vol. 174, 1991, pp. 96-101.
Derynck, et al., J. Biol. Chem., vol. 261, 1986, pp. 4377-4379.
Derynck, et al., Nature, vol. 316, 1985, pp. 701-705.
Sharples, et al., DNA, vol. 6, 1987, pp. 239-244.
de Martin, et al., The EMBO Journal, vol. 6, 1987, pp. 3673-3677.
Marquardt, et al., J. Biol. Chem., vol. 262, 1987, pp. 12127-12131.
Ten Dijke, et al., Proc. Natl. Acad. Sci., 85, 1988, pp. 4715-4719.
Cheifetz, et al., Cell, vol. 48, pp. 409-415.
Schlunegger, et al., Nature, vol. 358, 1992, pp. 430-434.
Urushizaki, et al., Tumor Res. vol. 22, 1987, pp. 41-55.
Holley, et al., Proc. Natl. Acad. Sci, USA, vol. 77, 1980, pp. 5989-5992.
Ristow, H.J., Proc. Natl. Acad. Sci, USA, vol. 83, 1986, pp. 5531-5533.
Jakowlew, et al., Molecular Endocrinology, vol. 2., 1988, pp. 1186-1195.

(Continued)

*Primary Examiner*—David S. Romeo
(74) *Attorney, Agent, or Firm*—E. Jay Wilusz; Peter J. Waibel

(57) ABSTRACT

The present invention relates to a folding process for the preparation of biologically active, dimeric, TGF-β (Transforming Growth Factor type β)-like protein in a detergent-free folding buffer.

7 Claims, No Drawings

OTHER PUBLICATIONS

Kondaiah, et al., J. Biol. Chem., vol. 265, 1990, pp. 1089-1093.
Mason, et al., Biochem. and Biophys. Res. Comm., vol. 135, 1986, pp. 957-964.
Cate, et al., Cell, vol. 45, 1986, pp. 685-698.
Padgett, et al., Nature, vol. 35, 1987, pp. 81-84.
Weeks, et al., Cell, vol. 51, 1987, pp. 861-867.
Lyons, et al., Proc. Natl. Acad. Sci. USA, vol. 86, 1989, pp. 4554-4558.
Postlethwaite, et al., J. Exp. Med. vol. 165, 1987; pp. 251-256.
Bürk, R.R., Proc. Nat. Acad. Sci. USA, vol. 70, 1973, pp. 369-372.
Brown, et al., Journal of Immunology, vol. 139, 1987, pp. 2977-2983.
Graycar, et al., Molecular Endocrinology, vol. 3, 1989, pp. 1977-1986.
Goff, et al., Proc. Natl. Acad. Sci. USA, vol. 81, 1984, pp. 6647-6651.
Buell, et al., Nucleic Acids Research, vol. 13, 1985, pp. 1923-1938.
Van Leerdam, et al., Virology, vol. 123, 1982, pp. 19-28.
Remaut, et al., Gene, vol. 22, 1983, pp. 103-113.
Laemmli, U.K., Nature, vol. 227, 1970, pp. 680-685.
Birnboim, et al., Nucleic Acids Research, vol. 7, 1979, pp. 1513-1522.
Beggs, J.D., Molecular Genetics in Yeast, Alfred Benzon Symposium 16, Copenhagen, 1981, pp. 383-389.
Hinnen, et al., Proc. Natl. Acd. Sci. USA, vol. 75, 1978, pp. 1929-1933.
Knecht, et al., Anal. Chem. vol. 58, 1986, pp. 2375-2379.
Tucker, et al., Science, vol. 226, 1984, pp. 705-707.
Absher, et al., Journal of Immunological Methods, vol. 138, 1991, pp. 301-303.
Danielpour, et al., Journal of Cellular Physiology, vol. 138, 1989, pp. 79-86.
Kelley, et al., Experimental Lung Research, vol. 18, 1992, pp. 877-887.
Meager, A., Journal of Immunological Methods, vol. 141, 1991, pp. 1-14.
Mustoe, et al., Science, vol. 237, 1987, pp. 1333-1336.
Grove, et al., Arch Dematol Res, vol. 272, 1982, pp. 381-385.
Schultz, et al., Science, vol. 235, 1987, pp. 350-352.
Hoppe, et al., Biochemistry, vol. 28, 1989, pp. 2956-2960.
Chan, W.-C., Biochemistry, vol. 7, 1968, pp. 4247-4253.
Ahmed, et al., The Journal of Biological Chemistry, vol. 50, 1975, pp. 8477-8482.
Tandon, et al., The Journal of Biological Chemistry, vol. 262, 1987, pp. 4486-4491.
Tandon, et al., The Journal of Biological Chemistry, vol. 261, 1986, pp. 15615-15618.
Tandon, et al., Biochimica et Biophysica Acta, vol. 955, 1988 pp. 19-25.
Tandon, et al., The Journal of Biological Chemistry, vol. 264, 1989, pp. 9859-9866.
Creighton, et al., Methods in Enzymology, vol. 107, 1984, pp. 305-329.
Hjelmeland, et al., Analytical Biochemisty, vol. 130, 1983, pp. 72-82.
Hjelmeland, et al., Methods in Enzymology, vol. 104, 1984, pp. 305-318.
Helenius, et al., Methods in Enzymology, vol. 54, 1979, pp. 734-749.
Derynck, et al., The EMBO Journal, vol. 7, 1988, pp. 3737-3743.
Halenbeck, Appl. Microbiol. Biotechnol. 31:710 (1989).
Saxena, Biochemistry 9:5015 (1970).
Pigiet, Proc. Natl. Acad. Sci (USA) 83:7643 (1986).
Thannhauser, Biochemistry 24:7681 (1985).
Katalog Calbiochem, pp. 252, 341, 264, 265.
Roberts, Adv. Cancer REs. 51:107 (1988).
Sporn, J. Cell. Biol. 105:1039 (1987).
Ten Dijke, Bio/Technology 7:793 (1989).
Sporn, Science 233:532 (1986).
Roberts, Proc. Natl. Acad. Sci. (USA) 80:6264 (1983).
Reeck, Cell 50: 667 (1987).
King, Chem. Eng. News 30.4. 1989, 37-54.
Lewin, Science 237: 1570 (1987).
Database wpi section ch, week 8739, derwent, an 87-273817; JP A 62190199 Fujisawa Pharm Aug. 20, 1987, Abstract Onlly.

* cited by examiner

SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
      (A) LENGTH: 339 base pairs
      (B) TYPE: nucleic acid
      (C) STRANDEDNESS: double
      (D) TOPOLOGY: linear (ii) MOLECULE TYPE: cDNA to mRNA (iii) HYPOTHETICAL: NO (vii) IMMEDIATE SOURCE:
      (B) CLONE: E. coli LC137/pPLMu.hTGF-beta1 (DSM 5656)

(ix) FEATURE:
      (A) NAME/KEY: CDS
      (B) LOCATION:1..336
      (D) OTHER INFORMATION:/product= "human TGF-beta1"

(xi) SEQUENCE DESCRIPTION: SEQ ID NO: 1:

```
GCC CTG GAC ACC AAC TAT TGC TTC AGC TCC ACG GAG AAG AAC TGC TGC        48
Ala Leu Asp Thr Asn Tyr Cys Phe Ser Ser Thr Glu Lys Asn Cys Cys
 1               5                  10                  15

GTG CGG CAG CTG TAC ATT GAC TTC CGC AAG GAC CTC GGC TGG AAG TGG        96
Val Arg Gln Leu Tyr Ile Asp Phe Arg Lys Asp Leu Gly Trp Lys Trp
                20                  25                  30

ATC CAC GAG CCC AAG GGC TAC CAT GCC AAC TTC TGC CTC GGG CCC TGC       144
Ile His Glu Pro Lys Gly Tyr His Ala Asn Phe Cys Leu Gly Pro Cys
         35                  40                  45

CCC TAC ATT TGG AGC CTG GAC ACG CAG TAC AGC AAG GTC CTG GCC CTG       192
Pro Tyr Ile Trp Ser Leu Asp Thr Gln Tyr Ser Lys Val Leu Ala Leu
             50                  55                  60

TAC AAC CAG CAT AAC CCG GGC GCC TCG GCG GCG CCG TGC TGC GTG CCG       240
Tyr Asn Gln His Asn Pro Gly Ala Ser Ala Ala Pro Cys Cys Val Pro
 65                  70                  75                  80

CAG GCG CTG GAG CCG CTG CCC ATC GTG TAC TAC GTG GGC CGC AAG CCC       288
Gln Ala Leu Glu Pro Leu Pro Ile Val Tyr Tyr Val Gly Arg Lys Pro
                 85                  90                  95

AAG GTG GAG CAG CTG TCC AAC ATG ATC GTG CGC TCC TGC AAG TGC AGC       336
Lys Val Glu Gln Leu Ser Asn Met Ile Val Arg Ser Cys Lys Cys Ser
                100                 105                 110

TGA                                                                    339
```

(2) INFORMATION FOR SEQ ID NO: 2:

(i) SEQUENCE CHARACTERISTICS:
        (A) LENGTH: 112 amino acids
        (B) TYPE: amino acid
        (D) TOPOLOGY: linear (ii) MOLECULE TYPE: protein (xi) SEQUENCE DESCRIPTION: SEQ ID NO: 2:

```
Ala Leu Asp Thr Asn Tyr Cys Phe Ser Ser Thr Glu Lys Asn Cys Cys
 1               5                  10                  15

Val Arg Gln Leu Tyr Ile Asp Phe Arg Lys Asp Leu Gly Trp Lys Trp
                20                  25                  30

Ile His Glu Pro Lys Gly Tyr His Ala Asn Phe Cys Leu Gly Pro Cys
         35                  40                  45

Pro Tyr Ile Trp Ser Leu Asp Thr Gln Tyr Ser Lys Val Leu Ala Leu
             50                  55                  60

Tyr Asn Gln His Asn Pro Gly Ala Ser Ala Ala Pro Cys Cys Val Pro
 65                  70                  75                  80

Gln Ala Leu Glu Pro Leu Pro Ile Val Tyr Tyr Val Gly Arg Lys Pro
                 85                  90                  95

Lys Val Glu Gln Leu Ser Asn Met Ile Val Arg Ser Cys Lys Cys Ser
                100                 105                 110
```

(2) INFORMATION FOR SEQ ID NO: 3:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: cDNA to mRNA (vii) IMMEDIATE SOURCE:
        (B) CLONE: E. coli LC137/pPLMu.hTGF-beta2 (DSM5657)

(ix) FEATURE:
    (A) NAME/KEY: CDS
    (B) LOCATION:1..336
    (D) OTHER INFORMATION:/product= "human TGF-beta2"

(xi) SEQUENCE DESCRIPTION: SEQ ID NO: 3:

| | | | | | | | | | | | | | | | | |
|---|---|---|---|---|---|---|---|---|---|---|---|---|---|---|---|---|
| GCT | TTG | GAT | GCG | GCC | TAT | TGC | TTT | AGA | AAT | GTG | CAG | GAT | AAT | TGC | TGC | 48 |
| Ala | Leu | Asp | Ala | Ala | Tyr | Cys | Phe | Arg | Asn | Val | Gln | Asp | Asn | Cys | Cys | |
| | 115 | | | | 120 | | | | | 125 | | | | | | |
| CTA | CGT | CCA | CTT | TAC | ATT | GAT | TTC | AAG | AGG | GAT | CTA | GGG | TGG | AAA | TGG | 96 |
| Leu | Arg | Pro | Leu | Tyr | Ile | Asp | Phe | Lys | Arg | Asp | Leu | Gly | Trp | Lys | Trp | |
| | 130 | | | | | 135 | | | | 140 | | | | | | |
| ATA | CAC | GAA | CCC | AAA | GGG | TAC | AAT | GCC | AAC | TTC | TGT | GCT | GGA | GCA | TGC | 144 |
| Ile | His | Glu | Pro | Lys | Gly | Tyr | Asn | Ala | Asn | Phe | Cys | Ala | Gly | Ala | Cys | |
| 145 | | | | | 150 | | | | 155 | | | | | 160 | | |
| CCG | TAT | TTA | TGG | AGT | TCA | GAC | ACT | CAG | CAC | AGC | AGG | GTC | CTG | AGC | TTA | 192 |
| Pro | Tyr | Leu | Trp | Ser | Ser | Asp | Thr | Gln | His | Ser | Arg | Val | Leu | Ser | Leu | |
| | | | 165 | | | | 170 | | | | | 175 | | | | |
| TAT | AAT | ACC | ATA | AAT | CCA | GAA | GCA | TCT | GCT | TCT | CCT | TGC | TGC | GTG | TCC | 240 |
| Tyr | Asn | Thr | Ile | Asn | Pro | Glu | Ala | Ser | Ala | Ser | Pro | Cys | Cys | Val | Ser | |
| | | | 180 | | | | | 185 | | | | | 190 | | | |
| CAA | GAT | TTA | GAA | CCT | CTA | ACC | ATT | CTC | TAC | TAC | ATT | GGC | AAA | ACA | CCC | 288 |
| Gln | Asp | Leu | Glu | Pro | Leu | Thr | Ile | Leu | Tyr | Tyr | Ile | Gly | Lys | Thr | Pro | |
| | | 195 | | | | | 200 | | | | | 205 | | | | |
| AAG | ATT | GAA | CAG | CTT | TCT | AAT | ATG | ATT | GTA | AAG | TCT | TGC | AAA | TGC | AGC | 336 |
| Lys | Ile | Glu | Gln | Leu | Ser | Asn | Met | Ile | Val | Lys | Ser | Cys | Lys | Cys | Ser | |
| 210 | | | | | 215 | | | | | 220 | | | | | | |
| TAA | | | | | | | | | | | | | | | | 339 |

(2) INFORMATION FOR SEQ ID NO: 4:

(i) SEQUENCE CHARACTERISTICS:
        (A) LENGTH: 112 amino acids
        (B) TYPE: amino acid
        (D) TOPOLOGY: linear (ii) MOLECULE TYPE: protein (xi) SEQUENCE DESCRIPTION: SEQ ID NO: 4:

| | | | | | | | | | | | | | | |
|---|---|---|---|---|---|---|---|---|---|---|---|---|---|---|
| Ala | Leu | Asp | Ala | Ala | Tyr | Cys | Phe | Arg | Asn | Val | Gln | Asp | Asn | Cys | Cys |
| 1 | | | | 5 | | | | | 10 | | | | | 15 | |
| Leu | Arg | Pro | Leu | Tyr | Ile | Asp | Phe | Lys | Arg | Asp | Leu | Gly | Trp | Lys | Trp |
| | | 20 | | | | | 25 | | | | | 30 | | | |
| Ile | His | Glu | Pro | Lys | Gly | Tyr | Asn | Ala | Asn | Phe | Cys | Ala | Gly | Ala | Cys |
| | | | 35 | | | | | 40 | | | | | 45 | | |
| Pro | Tyr | Leu | Trp | Ser | Ser | Asp | Thr | Gln | His | Ser | Arg | Val | Leu | Ser | Leu |
| | 50 | | | | | 55 | | | | | 60 | | | | |
| Tyr | Asn | Thr | Ile | Asn | Pro | Glu | Ala | Ser | Ala | Ser | Pro | Cys | Cys | Val | Ser |
| 65 | | | | | 70 | | | | | 75 | | | | | 80 |
| Gln | Asp | Leu | Glu | Pro | Leu | Thr | Ile | Leu | Tyr | Tyr | Ile | Gly | Lys | Thr | Pro |
| | | | | 85 | | | | | 90 | | | | | 95 | |
| Lys | Ile | Glu | Gln | Leu | Ser | Asn | Met | Ile | Val | Lys | Ser | Cys | Lys | Cys | Ser |
| | | | | 100 | | | | | 105 | | | | | 110 | |

(2) INFORMATION FOR SEQ ID NO: 5:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: cDNA to mRNA (vii) IMMEDIATE SOURCE:
    (B) CLONE: E. coli LC137/pPLMu.hTGF-beta3 (DSM 5658)

(ix) FEATURE:
    (A) NAME/KEY: CDS
    (B) LOCATION:1..336
    (D) OTHER INFORMATION:/product= "human TGF-beta3"

(xi) SEQUENCE DESCRIPTION: SEQ ID NO: 5:

```
GCT TTG GAC ACC AAT TAC TGC TTC CGC AAC TTG GAG GAG AAC TGC TGT        48
Ala Leu Asp Thr Asn Tyr Cys Phe Arg Asn Leu Glu Glu Asn Cys Cys
            115                 120                 125

GTG CGC CCC CTC TAC ATT GAC TTC CGA CAG GAT CTG GGC TGG AAG TGG        96
Val Arg Pro Leu Tyr Ile Asp Phe Arg Gln Asp Leu Gly Trp Lys Trp
130                 135                 140

GTC CAT GAA CCT AAG GGC TAC TAT GCC AAC TTC TGC TCA GGC CCT TGC       144
Val His Glu Pro Lys Gly Tyr Tyr Ala Asn Phe Cys Ser Gly Pro Cys
145                 150                 155                 160

CCA TAC CTC CGC AGT GCA GAC ACA ACC CAC AGC ACG GTG CTG GGA CTG       192
Pro Tyr Leu Arg Ser Ala Asp Thr Thr His Ser Thr Val Leu Gly Leu
                165                 170                 175

TAC AAC ACT CTG AAC CCT GAA GCA TCT GCC TCG CCT TGC TGC GTG CCC       240
Tyr Asn Thr Leu Asn Pro Glu Ala Ser Ala Ser Pro Cys Cys Val Pro
            180                 185                 190

CAG GAC CTG GAG CCC CTG ACC ATC CTG TAC TAT GTT GGG AGG ACC CCC       288
Gln Asp Leu Glu Pro Leu Thr Ile Leu Tyr Tyr Val Gly Arg Thr Pro
                195                 200                 205

AAA GTG GAG CAG CTC TCC AAC ATG GTG GTG AAG TCT TGT AAA TGT AGC       336
Lys Val Glu Gln Leu Ser Asn Met Val Val Lys Ser Cys Lys Cys Ser
210                 215                 220

TGA                                                                    339
```

(2) INFORMATION FOR SEQ ID NO: 6:

(i) SEQUENCE CHARACTERISTICS:
        (A) LENGTH: 112 amino acids
        (B) TYPE: amino acid
        (D) TOPOLOGY: linear (ii) MOLECULE TYPE: protein (xi) SEQUENCE DESCRIPTION: SEQ ID NO: 6:

```
Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Trp Lys Trp
            20                  25                  30

Val His Glu Pro Lys Gly Tyr Tyr Ala Asn Phe Cys Ser Gly Pro Cys
        35                  40                  45

Pro Tyr Leu Arg Ser Ala Asp Thr Thr His Ser Thr Val Leu Gly Leu
    50                  55                  60

Tyr Asn Thr Leu Asn Pro Glu Ala Ser Ala Ser Pro Cys Cys Val Pro
65                  70                  75                  80

Gln Asp Leu Glu Pro Leu Thr Ile Leu Tyr Tyr Val Gly Arg Thr Pro
            85                  90                  95

Lys Val Glu Gln Leu Ser Asn Met Val Val Lys Ser Cys Lys Cys Ser
                100                 105                 110
```

(2) INFORMATION FOR SEQ ID NO: 7:

(i) SEQUENCE CHARACTERISTICS:

(A) LENGTH: 336 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "recombinant hybrid DNA of (vii) IMMEDIATE SOURCE:
        (B) CLONE: E. coli LC137/pPLMu.TGF-beta1(44/45)beta3

(ix) FEATURE:
        (A) NAME/KEY: mat_peptide
        (B) LOCATION:1..132
        (D) OTHER INFORMATION:/product= "N-terminal 44 amino
            acids of human TGF-beta1"

(ix) FEATURE:
        (A) NAME/KEY: mat_peptide
        (B) LOCATION:133..336
        (D) OTHER INFORMATION:/product= "C-terminal 68 amino
            acids of human TGF-beta3"

(ix) FEATURE:
        (A) NAME/KEY: CDS
        (B) LOCATION:1..336
        (D) OTHER INFORMATION:/product= "hybrid TGF-beta named
            TGF-beta1-3"

(xi) SEQUENCE DESCRIPTION: SEQ ID NO: 7:

```
GCC CTG GAC ACC AAC TAT TGC TTC AGC TCC ACG GAG AAG AAC TGC TGC        48
Ala Leu Asp Thr Asn Tyr Cys Phe Ser Ser Thr Glu Lys Asn Cys Cys
 1               5                  10                  15

GTG CGG CAG CTG TAC ATT GAC TTC CGC AAG GAC CTC GGC TGG AAG TGG        96
Val Arg Gln Leu Tyr Ile Asp Phe Arg Lys Asp Leu Gly Trp Lys Trp
                20                  25                  30

ATC CAC GAG CCC AAG GGC TAC CAT GCC AAC TTC TGC TCA GGC CCT TGC       144
Ile His Glu Pro Lys Gly Tyr His Ala Asn Phe Cys Ser Gly Pro Cys
         35                  40                  45

CCA TAC CTC CGC AGT GCA GAC ACA ACC CAC AGC ACG GTG CTG GGA CTG       192
Pro Tyr Leu Arg Ser Ala Asp Thr Thr His Ser Thr Val Leu Gly Leu
 50                  55                  60

TAC AAC ACT CTG AAC CCT GAA GCA TCT GCC TCG CCT TGC TGC GTG CCC       240
Tyr Asn Thr Leu Asn Pro Glu Ala Ser Ala Ser Pro Cys Cys Val Pro
 65                  70                  75                  80

CAG GAC CTG GAG CCC CTG ACC ATC CTG TAC TAT GTT GGG AGG ACC CCC       288
Gln Asp Leu Glu Pro Leu Thr Ile Leu Tyr Tyr Val Gly Arg Thr Pro
                 85                  90                  95

AAA GTG GAG CAG CTC TCC AAC ATG GTG GTG AAG TCT TGT AAA TGT AGC       336
Lys Val Glu Gln Leu Ser Asn Met Val Val Lys Ser Cys Lys Cys Ser
            100                 105                 110
```

(2) INFORMATION FOR SEQ ID NO: 8:

(i) SEQUENCE CHARACTERISTICS:
        (A) LENGTH: 112 amino acids
        (B) TYPE: amino acid
        (D) TOPOLOGY: linear (ii) MOLECULE TYPE: protein (xi) SEQUENCE DESCRIPTION: SEQ ID NO: 8:

```
Ala Leu Asp Thr Asn Tyr Cys Phe Ser Ser Thr Glu Lys Asn Cys Cys
 1               5                  10                  15

Val Arg Gln Leu Tyr Ile Asp Phe Arg Lys Asp Leu Gly Trp Lys Trp
                20                  25                  30

Ile His Glu Pro Lys Gly Tyr His Ala Asn Phe Cys Ser Gly Pro Cys
         35                  40                  45
```

```
Pro Tyr Leu Arg Ser Ala Asp Thr Thr His Ser Thr Val Leu Gly Leu
         50                  55                  60

Tyr Asn Thr Leu Asn Pro Glu Ala Ser Ala Ser Pro Cys Cys Val Pro
 65                  70                  75                  80

Gln Asp Leu Glu Pro Leu Thr Ile Leu Tyr Tyr Val Gly Arg Thr Pro
                 85                  90                  95

Lys Val Glu Gln Leu Ser Asn Met Val Val Lys Ser Cys Lys Cys Ser
                100                 105                 110
```

(2) INFORMATION FOR SEQ ID NO: 9:

(i) SEQUENCE CHARACTERISTICS:
        (A) LENGTH: 336 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "recombinant hybrid DNA (vii) IMMEDIATE SOURCE:
        (B) CLONE: E. coli LC137/pPLMu.TGF-beta2(44/45)beta3

(ix) FEATURE:
        (A) NAME/KEY: mat_peptide
        (B) LOCATION:1..132
        (D) OTHER INFORMATION:/product= "N-terminal 44 amino
            acids of human TGF-beta2"

(ix) FEATURE:
        (A) NAME/KEY: mat_peptide
        (B) LOCATION:133..336
        (D) OTHER INFORMATION:/product= "C-terminal 68 amino
            acids of human TGF-beta3"

(ix) FEATURE:
        (A) NAME/KEY: CDS
        (B) LOCATION:1..336
        (D) OTHER INFORMATION:/product= "hybrid TGF-beta2-3"

(xi) SEQUENCE DESCRIPTION: SEQ ID NO: 9:

```
GCT TTG GAT GCG GCC TAT TGC TTT AGA AAT GTG CAG GAT AAT TGC TGC      48
Ala Leu Asp Ala Ala Tyr Cys Phe Arg Asn Val Gln Asp Asn Cys Cys
 1               5                  10                  15

CTA CGT CCA CTT TAC ATT GAT TTC AAG AGG GAT CTA GGG TGG AAA TGG      96
Leu Arg Pro Leu Tyr Ile Asp Phe Lys Arg Asp Leu Gly Trp Lys Trp
                 20                  25                  30

ATA CAC GAA CCC AAA GGG TAC AAT GCC AAC TTC TGC TCA GGC CCT TGC     144
Ile His Glu Pro Lys Gly Tyr Asn Ala Asn Phe Cys Ser Gly Pro Cys
             35                  40                  45

CCA TAC CTC CGC AGT GCA GAC ACA ACC CAC AGC ACG GTG CTG GGA CTG     192
Pro Tyr Leu Arg Ser Ala Asp Thr Thr His Ser Thr Val Leu Gly Leu
         50                  55                  60

TAC AAC ACT CTG AAC CCT GAA GCA TCT GCC TCG CCT TGC TGC GTG CCC     240
Tyr Asn Thr Leu Asn Pro Glu Ala Ser Ala Ser Pro Cys Cys Val Pro
 65                  70                  75                  80

CAG GAC CTG GAG CCC CTG ACC ATC CTG TAC TAT GTT GGG AGG ACC CCC     288
Gln Asp Leu Glu Pro Leu Thr Ile Leu Tyr Tyr Val Gly Arg Thr Pro
                 85                  90                  95

AAA GTG GAG CAG CTC TCC AAC ATG GTG GTG AAG TCT TGT AAA TGT AGC     336
Lys Val Glu Gln Leu Ser Asn Met Val Val Lys Ser Cys Lys Cys Ser
                100                 105                 110
```

(2) INFORMATION FOR SEQ ID NO: 10:

(i) SEQUENCE CHARACTERISTICS:

(A) LENGTH: 112 amino acids
       (B) TYPE: amino acid
       (D) TOPOLOGY: linear (ii) MOLECULE TYPE: protein (xi) SEQUENCE DESCRIPTION: SEQ ID NO: 10:

Ala Leu Asp Ala Ala Tyr Cys Phe Arg Asn Val Gln Asp Asn Cys Cys
 1               5                  10                  15

Leu Arg Pro Leu Tyr Ile Asp Phe Lys Arg Asp Leu Gly Trp Lys Trp
            20                  25                  30

Ile His Glu Pro Lys Gly Tyr Asn Ala Asn Phe Cys Ser Gly Pro Cys
            35                  40                  45

Pro Tyr Leu Arg Ser Ala Asp Thr Thr His Ser Thr Val Leu Gly Leu
        50                  55                  60

Tyr Asn Thr Leu Asn Pro Glu Ala Ser Ala Ser Pro Cys Cys Val Pro
 65                  70                  75                  80

Gln Asp Leu Glu Pro Leu Thr Ile Leu Tyr Tyr Val Gly Arg Thr Pro
                85                  90                  95

Lys Val Glu Gln Leu Ser Asn Met Val Val Lys Ser Cys Lys Cys Ser
            100                 105                 110

(2) INFORMATION FOR SEQ ID NO: 11:

(i) SEQUENCE CHARACTERISTICS:
        (A) LENGTH: 336 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "recombinant hybrid DNA (vii) IMMEDIATE SOURCE:
        (B) CLONE: E. coli LC137/pPLMu.TGF-beta3(44/45)beta2

(ix) FEATURE:
        (A) NAME/KEY: mat_peptide
        (B) LOCATION:1..132
        (D) OTHER INFORMATION:/product= "N-terminal 44 amino
            acids of human TGF-beta3"

(ix) FEATURE:
        (A) NAME/KEY: mat_peptide
        (B) LOCATION:133..336
        (D) OTHER INFORMATION:/product= "C-terminal 68 amino
            acids of human TGF-beta2"

(ix) FEATURE:
        (A) NAME/KEY: CDS
        (B) LOCATION:1..336
        (D) OTHER INFORMATION:/product= "hybrid TGF-beta3-2"

(xi) SEQUENCE DESCRIPTION: SEQ ID NO: 11:

GCT TTG GAC ACC AAT TAC TGC TTC CGC AAC TTG GAG GAG AAC TGC TGT     48
Ala Leu Asp Thr Asn Tyr Cys Phe Arg Asn Leu Glu Glu Asn Cys Cys
 1               5                  10                  15

GTG CGC CCC CTC TAC ATT GAC TTC CGA CAG GAT CTG GGC TGG AAG TGG     96
Val Arg Pro Leu Tyr Ile Asp Phe Arg Gln Asp Leu Gly Trp Lys Trp
            20                  25                  30

GTC CAT GAA CCT AAG GGC TAC TAT GCC AAC TTC TGT GCT GGA GCA TGC    144
Val His Glu Pro Lys Gly Tyr Tyr Ala Asn Phe Cys Ala Gly Ala Cys
            35                  40                  45

CCG TAT TTA TGG AGT TCA GAC ACT CAG CAC AGC AGG GTC CTG AGC TTA    192
Pro Tyr Leu Trp Ser Ser Asp Thr Gln His Ser Arg Val Leu Ser Leu
        50                  55                  60

-continued

```
TAT AAT ACC ATA AAT CCA GAA GCA TCT GCT TCT CCT TGC TGC GTG TCC         240
Tyr Asn Thr Ile Asn Pro Glu Ala Ser Ala Ser Pro Cys Cys Val Ser
 65                  70                  75                  80

CAA GAT TTA GAA CCT CTA ACC ATT CTC TAC TAC ATT GGC AAA ACA CCC         288
Gln Asp Leu Glu Pro Leu Thr Ile Leu Tyr Tyr Ile Gly Lys Thr Pro
                 85                  90                  95

AAG ATT GAA CAG CTT TCT AAT ATG ATT GTA AAG TCT TGC AAA TGC AGC         336
Lys Ile Glu Gln Leu Ser Asn Met Ile Val Lys Ser Cys Lys Cys Ser
                100                 105                 110
```

(2) INFORMATION FOR SEQ ID NO: 12:

(i) SEQUENCE CHARACTERISTICS:
        (A) LENGTH: 112 amino acids
        (B) TYPE: amino acid
        (D) TOPOLOGY: linear (ii) MOLECULE TYPE: protein (xi) SEQUENCE DESCRIPTION: SEQ ID NO: 12:

```
Ala Leu Asp Thr Asn Tyr Cys Phe Arg Asn Leu Glu Glu Asn Cys Cys
 1                   5                  10                  15

Val Arg Pro Leu Tyr Ile Asp Phe Arg Gln Asp Leu Gly Trp Lys Trp
                 20                  25                  30

Val His Glu Pro Lys Gly Tyr Tyr Ala Asn Phe Cys Ala Gly Ala Cys
                 35                  40                  45

Pro Tyr Leu Trp Ser Ser Asp Thr Gln His Ser Arg Val Leu Ser Leu
                 50                  55                  60

Tyr Asn Thr Ile Asn Pro Glu Ala Ser Ala Ser Pro Cys Cys Val Ser
 65                  70                  75                  80

Gln Asp Leu Glu Pro Leu Thr Ile Leu Tyr Tyr Ile Gly Lys Thr Pro
                 85                  90                  95

Lys Ile Glu Gln Leu Ser Asn Met Ile Val Lys Ser Cys Lys Cys Ser
                100                 105                 110
```

(2) INFORMATION FOR SEQ ID NO: 13:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO: 13:

CCGGAATTCC GG                         12

PROCESS FOR THE PRODUCTION OF BIOLOGICALLY ACTIVE PROTEIN

This is a continuation of U.S. application Ser. No. 09/316,724, filed May 21, 1999, now abandoned which is a continuation of U.S. application Ser. No. 08/776,444, filed Jan. 24, 1997 (now abandoned).

The present invention relates to a folding process for the preparation of biologically active, dimeric TGF-β (Transforming Growth Factor type β)-like protein in a detergent-free folding buffer.

BACKGROUND OF THE INVENTION

TGF-β-like proteins, i.e. proteins of the TGF-β superfamily play a central role in many biological regulation pathways such as embryonal development or regeneration of tissue. They are very potent biological agents which can be used also therapeutically for a series of different purposes. The best known members of the TGF-β superfamily are the TGF-βs themselves.

TGF-β was originally purified to homogeneity from human platelets, human placenta and bovine kidney and identified as a homodimeric protein with a molecular mass of about 25.000 Da. First characterized by its ability to act synergistically with EGF or TGF-α to induce anchorage-independent growth of untransformed NRK cells, recently, TGF-β has been shown to exhibit numerous regulatory effects on a wide variety of both normal and neoplastic cells indicating the importance of this protein as a multifunctional regulator of cellular activity. Depending upon the cell or tissue type, and the presence or absence of other growth factors, TGF-β may either stimulate mitogenesis, cell proliferation and growth, or may effectively inhibit said processes, or may exhibit other actions like e.g. control of adipogenesis, myogenesis, chondrogenesis, osteogenesis und immune cell function, stimulation of chemotaxis, or induction or inhibition of differentiation. Many of the actions of TGF-β are related to the response of cells or tissues to stress or injury, and to the repair of resultant damage. After inflammation, TGF-β plays the major role in the formation of granulation tissue, increases the expression of genes associated with extracellular matrix formation such as fibronectin, collagen and several protease inhibitors and stimulates collagen-matrix contraction by fibroblasts, suggesting its possible role in connective tissue contraction.

Until now five distinct, however, functionally and structurally closely related TGF-βs designated as TGF-β1, TGF-β2, TGF-β3, TGF-β4 and TGF-β5 are described. The former three are also found in man.

All TGF-βs are synthesized as 390 to 412 amino acid precursors that undergo proteolytic cleavage to produce the mature forms, which consist of the C-terminal 112 amino acids. In their mature, biologically active forms, TGF-βs are acid- and heat-stable disulfide-linked homodimers of two polypeptide chains of 112 amino acids each. The complete amino acid sequences of human (Derynck, R. et al. (1985) Nature 316, 701–705), murine (Derynck, R. et al. (1986) J. Biol. Chem. 261, 4377–4379) and simian TGF-β1 (Sharples, K. et al. (1987) DNA 6, 239–244) show remarkable sequence conservation, differing only in a single amino acid residue. Comparison of the amino acid sequence of human TGF-β1, human TGF-β2 (deMartin, R. et al. (1987) EMBO J. 6, 3673–3677; Marquardt, H. et al. (1987) J. Biol. Chem. 262, 12127–12131) and human TGF-β3 (Ten Dijke, P. et al. (1988) PNAS 85, 4715–4719) has demonstrated that the three proteins exhibit in their mature forms about 70–80% sequence identity. A heterodimeric TGF-β1.2 has been isolated from porcine platelets and consists of one subunit of TGF-β1 disulfide-linked to one subunit of TGF-β2 (Cheifetz, S. et al. (1987) Cell 48, 409–415).

Recently, attempts have been undertaken aiming to produce TGF-βs by means of recombinant techniques rather than isolating these factors from natural sources (e.g. platelets) in order to obtain sufficient amounts for testing in various therapeutic modalities. However, it has proven to be extremely difficult to obtain biologically active recombinant TGF-β. As can be seen from the sequences depicted in the sequence listing under SEQIDNos.1 to 6, the 112 amino acids containing mature forms of TGF-β1, TGF-β2 and TGF-β3 contain 9 cysteine residues. As has been shown for TGF-β2 the 9 cysteine residues are forming 4 intrachain and 1 interchain disulfide bonds [Schlunegger, M. P. and Gruetter, M. G., Nature 358:430–434(1992)]. Heterologous expression of TGF-β may lead to a product which, although having the correct primary structure, fails to fold properly to produce the correct secondary or tertiary structures and which, therefore, lacks the biological activity.

Taking the complexity of the native TGF-β molecules into account, it has generally been considered expedient to express the respective TGF-β genes in cells derived from higher organisms. Although expression of recombinant TGF-βs can be achieved in eukaryotic systems, the yields of biologically active, correctly folded material obtained are still far from being satisfactory.

Therefore, attempts were made to produce biologically active TGF-β in a microbial host. However, in e.g. bacteria the intracellular conditions are not conducive to correct folding, disulfide bond formation and disulfide-stabilized dimerization which is apparently essential for activity. Thus, only very little biologically active TGF-β could be obtained after expression of the respective gene in *E. coli* under the control of the lambda promoter as described in European Patent Application EP-A-0 268 561. Another report describes the expression of a TGF-β cDNA in *E.coli* under the control of the trp promoter yielding a radioactively labelled protein band with an apparent molecular weight of 13'000 Da in an autoradiogram of a SDS polyacrylamide gel, but no activity was measured (Urushizaki, Y. et al. (1987) Tumor Res. 22, 41–55).

When recombinant proteins are produced at high levels in bacterial (such as *E. coli*) expression systems, they often appear in the form of highly insoluble intracellular precipitates referred to as inclusion bodies or refractile bodies which can be recognized as bright spots visible within the enclosure of the cells under a phase contrast microscope. These inclusion bodies, which can readily be separated from the soluble bacterial proteins, contain the recombinant protein in a mostly denatured and reduced form which does not exhibit the functional activity of its natural counterpart and which therefore is useless as a commercial product. It is therefore generally agreed, that the recombinant refractile protein has to be solubilized under conditions which are suitable in maintaining it in its denatured form and subsequently has to be folded in order to undergo the transition from the denatured unfolded form to the proper, functionally active three-dimensional structure, the conformation of which is stabilized by relatively weak interatomic forces such as hydrogen bonding, hydrophobic interactions and charge interactions. In the case of cysteine containing proteins this process may also involve formation of disulfide bonds. When the formation of disulfide bonds is chemically promoted, the formation of incorrect intramolecular and, in the case of dimeric or multimeric proteins, intermolecular bridges should be prevented or at least minimized, since the formation of undesired, incorrectly folded isomers may yield non-homogenous material, thus complicating the further purification of the protein having the desired structure, or may generate a protein with reduced activity.

Folding of proteins usually is performed in a multistep process comprising the solubilization of the protein under strongly denaturing conditions, and then reducing the concentration of the chaotrop in order to allow the folding of the protein. However, such an approach failed in the folding of TGF-β. In the European patent application EP-A-0 433 225 a successful process for the production of biologically active, dimeric TGF-β-like protein is described, in which a mild detergent is used which allows the folding of the TGF-β-like protein while the detergent is present in the folding buffer.

It is known from the prior art (Tam et al., J. Am. Chem. Soc. 113:6657–6662, 1991) that dimethyl sulfoxide (DMSO) can be used for promoting a selective and efficient formation of disulfide bonds in peptides. The method is selective, i.e. without side reactions, and a wide pH range can be applied. However, correct disulfide bridge formation was shown only for peptides up to about 30 amino acids. In another publication (Bentle et al., U.S. Pat. No. 4,731,440) dimethylsulfone or a mixture of dimethylsulfone and urea was used for solubilization of somatotropin from inclusion bodies. The solubilized protein then could be renatured by contacting the dimethylsulfone containing solution of the protein with a mild oxidizing agent.

Surprisingly it was now found that TGF-β-like proteins can be refolded into the active, dimeric form by treating the solubilized monomer with a detergent-free folding buffer which comprises an organic solvent such as e.g. DMSO, DMF or a mixture of DMSO and DMF.

OBJECT OF THE INVENTION

It is the object of the present invention to provide an improved process for the production of biologically active, dimeric TGF-β-like protein from its denatured or otherwise non-native form. This object is achieved by the unexpected finding that considerable amounts of the desired dimeric product can be obtained in an unexpected yield when the monomeric form of said protein is treated with a detergent-free folding buffer which comprises an organic solvent such as e.g. DMSO, DMF or a mixture of DMSO and DMF.

DETAILED DESCRIPTION OF THE INVENTION

The present invention relates to an improved process for the production of a dimeric, biologically active Transforming Growth Factor type β (TGF-β)-like protein, comprising subjecting the denatured, monomeric form of said TGF-β-like protein to detergent-free folding conditions.

The term "TGF-β-like protein" in context with the present invention means a protein having in its monomeric form a sequence with at least 75% homology to at least one of the amino acid sequences of a monomer of the following members of the TGF-β superfamily:

TGF-β1, TGF-β2 and TGF-β3; a growth inhibitor isolated from conditioned medium of BSC-1 monkey kidney cells (i.e. polyergin; Holley, R. W. et al. (1980) PNAS 77, 5989–5992; Ristow, H. J. (1986) PNAS 83, 5531–5533); TGF-β4 from chicken embryo chondrocytes (Jakowlew, S. B. et al. (1988) Molecular Endocrinology2, 1186–1195); TGF-β5 from Xenopus-Laevis (Kondaiah, P. et al. (1990) J. Biol. Chem. 265, 1089–1093); TGF-β-related inhibins and activins (gonadal proteins that regulate pituitary secretion of follicle stimulating hormone); Mullerian inhibiting substance (MIS, which inhibits the development of the Mullerian duct in mammalian male embryos); bone morphogenic proteins (BMP, a group of polypeptides involved in the induction of cartilage and bone formation; the members of this group known today are BMP-2, BMP-3, BMP-4, BMP-5, BMP-6, BMP-7, BMP-8 and BMP-9); the transcript from the decapentaplegic gene complex of Drosophila (dpp, which acts to control morphogenesis in the fly embryo); Vg-1 (the product of the Xenopus transcript which is present in the vegetal pole of oocytes); and Vgr-1, a Vg-1 related mammalian gene (Mason, A. et al. (1986) Biochem. Biophys. Res. Commun. 135, 957–964; Cate, R. et al. (1986) Cell 45, 685–698; Wozney, J. M. et al. (1988) Science 242, 1528–1534; Padgett, R. et al. (1986) Nature 325, 81–84; Weeks, D. L. and Melton, D. A. (1987) Cell 51, 861–868; Lyons, K. et al. (1989) PNAS 86, 4554–4558).

Also included within the meaning of "TGF-β-like protein" are heterodimers containing subunits of different TGF-β like proteins, or fragments and mutants of the above mentioned proteins which retain one or all of the biological activities of the parent molecule.

In a preferred meaning the term "TGF-β-like protein" in context with the present invention represents any protein of the TGF-β superfamily. In a more preferred meaning it represents a protein selected from the group consisting of the following proteins of the TGF-β superfamily: TGF-β1, TGF-β2 and TGF-β3 of mammalian such as human or animal origin, e.g. simian, murine, porcine, equine or bovine, as well as heterodimeric TGF-βs consisting of two different subunits of 112 amino acids each, and fragments and mutants of a TGF-β1 including hybrid molecules in which parts of different TGF-βs are exchanged; a growth inhibitor isolated from conditioned medium of BSC-1 monkey kidney cells (i.e. polyergin); TGF-β4 from chicken embryo chondrocytes; TGF-β5 from Xenopus-Laevis; TGF-β-related inhibins and activins (gonadal proteins that regulate pituitary secretion of follicle stimulating hormone); Mullerian inhibiting substance (MIS, which inhibits the development of the Mullerian duct in mammalian male embryos); bone morphogenic proteins (BMP, a group of polypeptides involved in the induction of cartilage and bone formation; the members of this group known today are BMP-2, BMP-3, BMP-4, BMP-5, BMP-6, BMP-7, BMP-8 and BMP-9); the transcript from the decapentaplegic gene complex of Drosophila (dpp, which acts to control morphogenesis in the fly embryo); Vg-1 (the product of the Xenopus transcript which is present in the vegetal pole of oocytes); and Vgr-1, a Vg-1 related mammalian gene. Also included within the meaning of "TGF-β-like protein" are heterodimers containing subunits of different TGF-β1 like proteins, or fragments and mutants of the above mentioned proteins which retain one or all of the biological activities of the parent molecule.

Even more preferred TGF-β-like proteins are selected from the group consisting of TGF-β1, TGF-β2, TGF-β3, heterodimeric TGFβs, fragments and mutants of a TGF-β1 including hybrid molecules in which parts of different TGF-βs are exchanged, BMPs, inhibins and activins. Even more preferred are BMP-2, TGF-β1, TGF-β2 and TGF-β3, and heterodimers and fragments and mutants thereof including hybrid molecules in which parts of the different TGF-βs are exchanged, preferably preferentially hybrid TGF-β1-3, hybrid TGF-β2-3 and hybrid TGF-β3-2 or TGF-β1-2 consisting, in N- to C-terminal order, of the N-terminal 44 amino acids of human TGF-β1 and of the C-terminal 68 amino acids of TGF-β2. Even more preferred TGF-β-like proteins are those having the amino acid sequences depicted in the sequence listing under SEQID No.1, 3, 5, 7, 9 or 11. The most preferred TGF-β-like protein is TGF-β3.

The biological activity of TGF-β for the purpose herein is defined as either
- the cell migration promoting activity of TGF-β on fibroblasts, (Postlethwaite, A. E. et al. (1987) J. Exp. Med. 165,251, modified according to Burk, R. (1973) PNAS 70,369),
- the inhibitory effect of TGF-β on the growth of human A 375 melanoma cells (Brown, T. J. et al. (1987) J. Immunol. 139, 2977),
- inhibition of CCL-64 cell DNA synthesis assay (Graycar, J. L. etal., (1989) Molecular Endocrinology 3:1977–1986) or
- inhibition of the growth of a continuous mink lung epithelial cell line Mv-1-Lu (ATCC/CCL64) as described in the Examples hereinafter.

Monomeric TGF-β-like protein derived from any source or method can be folded into the corresponding dimeric, biologically active TGF-β-like protein according to the present method. For example, the monomeric form of the TGF-β-like protein can be derived from a natural source or produced by means of recombinant DNA technology or synthetically by methods well known in the art. In the case the monomer is not suitable for in vitro folding due to contaminants, the solubilized and denatured monomer can be purified by chromatography, e.g. by size exclusion chromatography on e.g. Sephacryl S-100 HR.

Before being folded, the monomeric TGF-β-like protein has to be present in a denatured (i.e. unfolded), solubilized form. Capable of effectively denaturing and solubilizing proteins are so-called chaotropic agents well known in the art, which, in aqueous solution and in suitable concentrations, change the spatial configuration of the respective protein through alterations at the surface thereof, either through altering the state of hydration, the solvent environment, or the solvent-surface interaction. Examples of such chaotropic agents or denaturants include urea, guanidine hydrochloride, sodium thiocyanate at concentrations in the range of about 4 to about 9 M, and detergents such as SDS, which are supplied in concentrations in the order of 0.01 to 2 percent. Also, acidification of the aqueous solution containing the TGF-β-like protein to a pH of about 2 to about 4, e.g. with a low molecular weight aliphatic organic acid, preferably having 2, 3 or 4 C-atoms, more preferably acetic acid, as well as basic conditions of e.g. pH 10 and above and elevated temperatures will result in denaturation and solubilization of the monomer.

The monomer is then made subject to "folding conditions" which allow the recovery of the biologically active dimer. The term "folding conditions" refers to conditions under which intra- and interchain disulfide bond formation is promoted and the denatured monomer is permitted to assume a conformation associated with the biological activity. This process does not involve any change in the primary structure (i.e. the amino acid sequence) of the monomer, but relates to the formation of the three-dimensional conformation of the dimeric product which is associated with the biological activity. This process includes the formation of disulfide bonds and the association of monomers into a dimeric, biologically active structure.

For this purpose the denatured monomer is according to the present invention treated with a folding buffer which comprises an organic solvent. Preferred organic solvents are selected from the group consisting of DMSO, dimethylsulfone (DMSO$_2$), DMF and any mixture of two or three members of the group consisting of DMSO, DMSO$_2$, and DMF. Preferred organic solvents are selected from the group consisting of DMSO, DMF and any mixture therof.

Folding may be performed at a neutral or alkaline pH and at a reasonable temperature, e.g. between about 0° C. and about 40° C. A preferred pH is between about 7 and about 10, more preferred in the case of DMSO is about pH 9 to 9.5 and in the case of DMF is about pH 8.5.

Conventional buffer systems which can be used for folding according to the present invention are buffers which provide sufficient buffer capacity between pH 6 and 10. All buffers that have no inhibiting effect on the folding of proteins are applicable in the present invention.

For example, suitable buffers are Tris, bis-Tris or piperazine buffers. The buffers may contain additionally a salt, if desired, and a basic amino acid, if desired.

Salts which can be used in the folding buffer are, for example, salts of $Na^+$, $Li^+$, $K^+$, $NH_4^+$, $Mg^{2+}$, $Ca^{2+}$, or $Mn^{2+}$ with $Cl^-$, $F^-$, $Br^-$, $J^-$, $HCO_3^-$, $SO_4^{2-}$, phosphate, acetate, cyanate or rhodanid, or other alkali metal—or alkaline earthmetal—halogen or pseudohalogen compounds at a concentration of up to 3 M. Preferred is NaCl at a concentration of 1 to 2 M.

A basic amino acid which can be used in the folding buffer is, for example, arginine, preferably in a concentration of 0.5 M.

For folding according to the present invention DMSO can be used in a concentration of about 10 to about 50%, more preferably about 20 to about 50%, even more preferably about 30 to about 50%, most preferably about 40%.

DMSO in the folding buffer can be replaced by DMF. DMF can be used in a concentration of about 10 to about 50%, more preferably about 20 to about 50%, even more preferably about 30 to about 50%, most preferably about 30 to about 40%.

A mixture of DMSO and DMF can be used in a concentration of about 10 to about 50% for both solvents combined.

DMSO or DMF can accordingly also be replaced by DMSO$_2$.

In a preferred embodiment of the present invention the folding buffer additionally contains a reducing substance. A suitable reducing substance which encourages the formation of disulfides in proteins or peptides is e.g. a low molecular weight sulfhydryl reagent selected from the group consisting of glutathione in its reduced form, dithiothreitol in its reduced form, β-mercaptoethanol in its reduced form, mercaptomethanol in its reduced form, cysteine and cysteamine. A suitable concentration is e.g. about 1 to 100 mM, preferably about 1 to 10 mM, more preferably about 2.5 mM Preferred reduced sulfhydryl compounds for use in the present invention are selected from the group consisting of reduced glutathione, cystein, cysteamin, and β-mercaptoethanol. Reduced glutathione is the most preferred compound.

The folding is performed at reasonable temperatures, for example between about 0 and about 40° C., preferably at about 4° C., and for a reasonable time period, for example between about 2 and about 720 h. Since the duration of the folding depends on the temperature used, the temperature may be optimized for any desired folding time period and vice versa.

The production of a dimeric, biologically active TGF-β-like protein according to the present invention may be performed in a one step procedure, wherein the monomer of said protein is transferred to the folding buffer and the reaction mixture is incubated for a time period of e.g. 2 hours up to 7 or more days at a temperature between e.g. 0° C. and 40° C., preferably 4° C. while folding and dimerization continuously take place. The protein concentration during the folding reaction is of considerable importance since when being too high, the monomers might undergo substantial aggregation leading to the formation of undesired higher-order oligomers. Final yields of dimeric product are increased, if the protein concentration is less than about 2 mg/ml, a concentration range of 0.01 to 0.5 mg/ml is preferred.

After folding, the biologically active dimer is purified in order to remove incompletely folded TGF-β-like protein and impurities, in particular, pyrogens or other endotoxins which might be present in the preparation if the polypeptide was produced in microbial host cells. Separation of the dimer is performed by chromatography such as sizing gel chromatography, hydrophobic interaction chromatography or ion exchange chromatography, e.g. on a Mono S column and reverse phase HPLC.

The present invention further relates to dimeric biologically active TGF-β-like proteins when produced according to the process of the invention. These TGF-β-like proteins can be used in a variety of therapeutic modalities.

The following examples illustrate the invention without being meant to be limitative.

EXAMPLE 1

Expression of TGF-β1, TGF-β2 and TGF-β3 in *E. coli*

EXAMPLE 1A

General Methods

Bacterial strain:
  *E. coli* K12/LC 137: $htpR_{am}$, $lon_{R9}$, $lac_{am}$, $mal_{am}$, $trp_{am}$, $pho_{am}$, rspL, tsx::Tn10, $supC_{ts}$ (Goff, S. A. et al. (1984) PNAS 81, 6647–6651).

Plasmids:
  pPLMu (Buell, G. et al. (1985) Nucleic Acids Res. 13, 1923–1938): This plasmid carries the bacteriophage $\lambda P_L$ promoter with the phage Mu ner gene ribosome binding site (Van Leerdam, E. et al. (1982) Virology 123, 19–28).
  $pcI_{857}$: Plasmid encoding a thermolabile $\lambda CI_{857}$ repressor and conferring resistance to kanamycin (Remault, E. et al. (1983) Gene 22, 103–113).

SDS Gel-electrophoresis:
  SDS polyacrylamide gel-electrophoresis (SDS-PAGE) and protein staining is done as described previously (Laemmli, U. K. (1970) Nature 227, 680–685) using the Miniprotean II cell from BIORAD and 1 mm thick 18% polyacrylamide gels.

Heat Induction:
  7 ml of LB-Medium (Maniatis et al. (1982), Molecular Cloning, Cold Spring Harbor Laboratory, New York) in a 20 ml culture tube containing 40 82 g of each ampicillin and kanamycin (LB/amp/kan) are inoculated with a single colony and incubated with shaking overnight at 30° C. 5 ml of this overnight culture are added to 15 ml of LB/amp/kan in a 100 ml Erlenmeyer flask. This flask is transferred to a 42° C. waterbath shaker. A 2 ml sample is taken before transfer (non-inducing conditions) and 1 ml samples at 1 hour intervals after the transfer (inducing conditions). Cells are pelleted by centrifugation (5 min, 10,000 rpm in an Eppendorf centrifuge) and the supernatant is discarded. The pellet is resuspended in 100 μl of sample buffer for SDS-PAGE and heated for 10 min at 95° C. 5 μl aliquots are loaded for SDS-PAGE.

Preparation of Competent Cells:
  Competent *E. coli* cells are prepared by the calcium chloride procedure as described in Maniatis et al. (1982), Molecular Cloning, Cold Spring Harbor Laboratory, New York Cells carrying plasmid $pcI_{857}$ are grown at 30° C.

EXAMPLE 1B

Construction of Expression Vectors pPLMu.hTGF-β1, pPLMu.hTGF-β2 and pPLMu.hTGF-β3 and expression of TGF-β1, TGF-β2 and TGF-β3

The coding sequences of TGF-β1, TGF-β2 and TGF-β3 (shown in the sequence listing), respectively, are cloned into plasmid PGem-5ZF(+) (Promega) digested with NcoI, dephosphorylated with Calf Intestinal Alkaline Phosphatase (Boehringer) and filled in with Klenow polymerase (Gibco-BRL). The resulting constructs are designated as pGKM 125 (TGF-β1), pGKM 740 (TGF-β2) and pGKM 126 (TGF-β3) and are used to transform competent *E. coli* Y 1090 cells. Clones carrying the correct inserts encoding TGF-β1, TGF-β2 and TGF-β3 are designated as *E. coli* Y1090/pGKM 125 (TGF-β1), *E. coli* Y1090/pGKM 740 (TGF-β2) and *E. coli* Y1090/pGKM 126 (TGF-β3), respectively.

*E. coli* Y1090/pGKM 125, *E. coli* Y1090/pGKM 740 and *E. coli* Y1090/pGKM 126 cells are grown in LB medium and plasmid DNA is prepared by the method of Bimboim, H. C. and Doly, H. (1979) Nucleic Acids Research 7, 1513. 5 μg of plasmid DNA are cut to completion in 50 μl restriction buffer with either NcoI and SalI (pGKM125), NcoI and EcoRV (pGKM740) or NcoI alone (pGKM126) following the recommendations of the supplier (Boehringer). The DNA is precipitated by addition of 5 μl 3 M sodium acetate, 100 mM $MgCl_2$, 5 mM EDTA and 150 μl ethanol. After incubation at −70° C. for 15 min the DNA is pelleted by centrifugation at 13.000 g for 15 min in a SS34 rotor in a Sorvall centrifuge. The supernatant is discarded and the pellet is resuspended in 80 μl 0.089 M TRIS borate, 0.089 M boric acid and 0.002 M EDTA (TBE buffer) containing 0.25% bromphenol blue and 0.25% xylene cyanol. 4 times 20 μl samples are electrophoresed through a 1% agarose gel in TBE buffer containing 0.5 μg/ml ethidium bromide at 50 volts till the bromphenol blue marker reaches the bottom of the 10 cm long and 0.8 cm thick gel. The DNA fragments coding for mature TGF-β1, TGF-β2 and TGF-β3, respectively, are visualized under short wave UV light, cut out with a razor blade and electroeluted from the gel piece in a Schleicher & Schüll Biotrap apparatus applying 200 mamp for 1.5 hours. The eluted DNA fragments are precipitated (see above) and resuspended in 20 μl TE.

5 μl of plasmid pPLMu are linearized by digestion with either NocI and SalI, NocI and EcoRV or NocI alone and gel purified as described above for the fragment DNAs. 100 ng of the linearized and purified pPLMu vector DNA and 3 times the molar equivalent of the respective purified fragment DNA are incubated at 4° C. for 15 hours in 20 μl of ligation buffer (70 mM TRIS/HCl, pH 7.5, 10 mM MgCl2, 5 mM DTT, 0.1 mM adenosine-triphos-phate) containing 1 unit of DNA ligase (Boehringer).

10 μl of the ligation mixture are added to 200 μl of cold (40° C.) competent *E. coli* LC 137 cells carrying plasmid pcI$_{857}$. After 30 min the cells are heat shocked by incubation for 1.5 min in a 42° C. water bath. 2 ml of LB medium are added and the culture is shaken for 60 min at 30° C. 200 μl aliquots are plated on LB plates containing ampicillin and kanamycin and incubated for 22 hours at 30° C. Single colonies are cultivated and plasmid DNA is analysed. Subcloning of the DNA fragments coding for TGF-β1, TGF-β2 and TGF-β3 in pPLMu results in plasmids pPLMu.hTGF-β1, pPLMu.hTGF-β2 and pPLMu.hTGF-β3, respectively. Clones containing the above constructs are referred to as *E. coli* LC 137/pPLMu.hTGF-β1, *E. coli* LC 137/pPLMu-.hTGF-β2 and *E. coli* LC 137/pPLMu.hTGF-β3, respectively.

*E. coli* LC 137/pPLMu.hTGF-β1, *E. coli* LC 137/pPL-Mu.hTGF-β2 and *E. coli* LC 137/pPLMu.hTGF-β3 cells are heat induced (see example 1A) and the expressed proteins are analysed by SDS-PAGE. TGF-β1, TGF-β2 and TGF-β3 all appear as heat induced proteins 2 hours after heat induction migrating with an apparent molecular mass of approximately 12.000 Da.

EXAMPLE 1C

Fermentation of Transformants

Overnight cultures of *E. coli* LC137/pPLMu.h.TGF-β1, *E.coli*LC137/pPLMu.h.TGF-β2 and *E.coli* LC137/pPLMu-.h.TGF-β3 in 2l Erlenmeyer flasks containing 750 ml of LB medium with 40 mg/l of ampicillin and kanamycin are grown at 30° C. 300 ml of the overnight cultures are added to 750 ml of LB medium containing antibiotics as mentioned above in 2 l Erlenmeyer flasks and heated to 42° C. by shaking for approximately 3.5 minutes in a 65° C. water bath. The flasks are then transferred to a 42° C. shaker and incubated for 3 hours. The flasks are cooled down to 12° C. in an ice water bath and the cells are collected after centrifugation for 10 minutes at 8.000 rpm in a GSA rotor (Sorvall).

EXAMPLE 2

Expression of TGF-β1, TGF-β2 and TGF-β3 in *Saccharomyces cerevisiae*

The coding sequences of mature TGF-β1, TGF-β2 and TGF-β3 are expressed in *Saccharomyces cerevisiae* under the control of the inducible promoter of the yeast acid phosphatase (PH05).

The expression vectors are constructed in two steps:
A. construction of plasmid pJDB207/PH05-RIT 12,
B. construction of plasmids pJDB207R/PH05-TGF-β1, pJDB207R/PH05-TGF-β2 and pJDB207R/PH05-TGF-β3, where A) provides the yeast vector and the PH05 transcriptional terminator and B) provides the expression cassettes with an insert coding for mature TGF-β1, TGF-β2 and TGF-β3, respectively, under the control of the PH05 promoter.

EXAMPLE 2A

Construction of Plasmid pJDB207/PH05-RIT 12

Plasmid p31 RIT 12 (European patent application EP 277.313) is linearized with restriction endonuclease SalI. Partial HindIII digestion in the presence of ethidiumbromide results in a 1 kb SalI/HindIII fragment comprising the 276 bp SalI/BamHI pBR322 sequence, the 534 bp promoter of the yeast acid phosphatase PH05, the yeast invertase signal sequence (coding for 19 amino acids) and the PH05 transcriptional terminator.

The 1 kb SalI/HindIII fragment of p31 RIT 12 is cloned in to the yeast-*E.coli* shuttle vector pJDB207 (Beggs, J. D. in: Molecular Genetics in yeast, Alfred Benzon Symposium 16, Copenhagen, 1981, pp.383–389), which had been cut with SalI and HindIII. The resulting plasmid containing the 1 kb insert is referred to as pJDB207/PH05-RIT 12.

EXAMPLE 2B

Construction of Plasmid pJDB207R/PH05-TGF-β3

Plasmid pGKM740 (TGF-β3) (see example 1.G) is cut with NocI. The sticky ends are filled in a reaction with Klenow DNA polymerase. EcoRI linker (5'-CCGGAATTC-CGG; Biolabs) are added and the mixture is ligated. The resulting circular plasmid is referred to as pGKMA668 (TGF-β3) and is cut with EcoRI and SalI. A 0.4 kb EcoRI/SalI fragment is isolated from an agarose gel, purified and resuspended in sterile water at a concentration of 25 μg/ml. The fragment contains the mature coding sequence of TGF-β3 with an ATG in frame to codon GCT which defines amino acid Ala 1 of mature TGF-β3.

The PH05 promoter is isolated from plasmid p31 RIT 12 (see above) on a 534 bp BamHI/EcoRI fragment. Plasmid pJDB207/PH05-RIT 12 is cut with BamHI and XhoI. The large, 6.8 kb BamHI/XhoI fragment is isolated. The PH05 transcriptional terminator remains on the fragment. The BamHI/EcoRI PH05 promoter fragment, the EcoRI/SalI fragment coding for TGF-β3, and the BamHI/XhoI vector fragment are ligated. One correct clone with the TGF-β3 gene under the control of the PH05 promoter cloned in an anticlockwise orientation into pJDB207 is referred to as pJDB207R/PH05-TGF-β3.

In an analogous manner, mature TGF-β1 and TGF-β2 are expressed in *S. cerevisiae*. The plasmids containing the coding sequences of TGF-β1 and TGF-β3 are pGKM125 and pGKM126, respectively (see example 1.G). After digestion of these plasmids with NocI, addition of EcoRI linkers and ligation, the resulting circular plasmids are cut with EcoRI and SalI. The EcoRI/SalI fragments are cloned into pJDB207 as described above. The resulting plasmids are referred to as pJDB207R/PH05-TGF-β1 and pJDB207R/PH05-TGF-β3.

EXAMPLE 2C

Transformation of *S. cerevisiae* Strain GRF18

*Saccharomyces cerevisiae* strain GRF18 (MATα, his3-11, his3-15, leu2-3, leu2-112, can$^R$, DSM 3665) is transformed with plasmids
pJDB207R/PH05-TGF-β1
pJDB207R/PH05-TGF-β2
pJDB207R/PH05-TGF-β3 using the transformation protocol described by Hinnen, A.etal. (1978) PNAS 75,1929.

Transformed yeast cells are selected on yeast minimal medium plates deficient in leucine.

Single transformed yeast colonies are isolated and referred to as
*Saccharomyces cerevisiae* GRF18/pJDB207R/PH05-TGF-β1

Saccharomyces cerevisiae GRF18/pJDB207R/PH05-TGF-β2 and
Saccharomyces cerevisiae GRF18/pJDB207R/PH05-TGF-β3.

EXAMPLE 2D

Fermentation of S. cerevisiae Transformants and Preparation of Cell Extracts

The yeast transformants, as mentioned above, contain plasmids with PH05 promoter-controlled expression cassettes and therefore require derepression of the promoter for the expression of TGF-β1, TGF-β2 or TGF-β3. Transformants are each grown in two successive precultures (10 ml and 50 ml) in yeast high $P_i$ minimal medium prepared according to the recipe of the Difco Yeast Nitrogen Base without amino acids but containing 10 g/l L-asparagine instead of $(NH_4)_2SO_4$, 1 g/l L-histidine and 20 g/l glucose. The cells of the second preculture are washed in 0.9% NaCl and all the cells are used to inoculate 100 ml of low $P_i$ minimal medium prepared according to the recipe of the Difco Yeast Nitrogen Base medium (without amino acids), but containing 0.03 g/l $KH_2PO_4$, 10 g/l L-asparagine, 1 g/l L-histidine and 20 g/l glucose. The cultures are agitated at 30° C. at 180 rpm.

Cells from 10 ml of culture are collected at 5 h, 24 h and 48 h by centrifugation at 3000 rpm and washed once in 0.9% NaCl. The cell pellet is resuspended in lysis buffer [66 mM potassium phosphate pH 7.4, 4 mM Zwittergent (Calbiochem)]. 8 g of glass beads (0.5–0.75 mm in diameter) are added and the suspension is shaken vigerously 4–5 times for 2 min each on a Vortex Mixer in the cold. The cell extract is decanted to get rid of the glass beads. Cell debris in the extract are sedimented by centrifugation for 5 min at 3000 rpm at 4° C. The supernatant and pellets are separated and stored at −20° C.

EXAMPLE 3

EXAMPLE 3A

Recovery of Non-soluble, Monomeric TGF-β3 from E. coli

E. coli LC 137/pPLMu.hTGF-β3 cells are fermented as described in Example 1C. Cell disruption and recovery of non-soluble TGF-β3 is performed at 4° C. About 18 g of wet cells are suspended in 60 ml of 0.1 M TRIS/HCl, 10 mM EDTA, 1 mM PMSF (Phenyl Methan Sulphonyl Fluoride), pH 8.3 (disruption buffer). The cells are passed two times through a Frenchpress (SLM Instruments, Inc.) according to the manufacturers instructions and the volume is brought to 200 ml with the disruption buffer. The suspension is centrifuged for 20 min at 15.000 g. The pellet obtained is suspended in 100 ml disruption buffer containing 1 M NaCl and centrifuged for 10 min as above. The pellet is suspended in 100 ml disruption buffer containing 1% Triton X-100 (Pierce) and again centrifuged for 10 min as above. The washed pellet is then suspended in 50 ml of 20 mM Tris/HCl, 1 mM EDTA, 1 mM PMSF, 1 % DTT and homogenised in a Teflon tissue grinder. The resulting suspension contains crude monomeric TGF-β3 in a non-soluble form.

EXAMPLE 3B

Solubilization and Purification of Monomeric TGF-β3

10 ml of the TGF-β3 suspension obtained according to Example 3A are acidified with 10% acetic acid to pH 2.5 and centrifuged in an Eppendorf centrifuge for 10 min at room temperature. The supernatant is chromatographed on a Sephacryl S-100 column (Pharmacia, 2.6×78 cm) in 10% acetic acid at a flow rate of 1.4 ml/min. (Alternatively, the chromatography can be performed on Sephacryl S-100HR (Pharmacia) and the column can be run in 1% acetic acid or 5 mM HCl, respectively.) Fractions containing monomeric, denatured TGF-β3 eluting between 190 min and 220 min are pooled. This material is used for folding to get biologically active, dimeric TGF-β3 (Example 4) or for further purification and structural analysis (Example 3D.).

EXAMPLE 3C

Recovery of Monomeric TGF-β3 from Saccharomyces cerevisiae

The pellet of broken cells obtained from a 500 ml fermentation performed as described above is suspended in 20 ml 4M urea, 0.1 M TRIS, 1% DTT, pH 8.0. The mixture is kept at room temperature for 30 minutes with intermittant vortexing every 5 minutes. Insoluble material is removed by centrifugation at 30'000 g for 30 minutes at 4° C. and the supernatant is adjusted to pH 2.5 with acetic acid and dialysed extensively against 5% acetic acid overnight at 4° C. The solution is centrifuged as above and the clear supernatant is concentrated by ultrafiltration on a YM 10 membrane (Amicon) to a final volume of 4 ml. The sample is then chromatographed on Sephacryl S-100 HR (Pharmacia) in 5% acetic acid as described in Example 3.B yielding monomeric TGF-β3.

EXAMPLE 3D

Further Purification of Monomeric TGF-β3 by RP-HPLC

Aliquots of the pooled fractions from the Sephacryl S-100 column (Example 3.B) are purified on a Vydac 214TP5415 HPLC reverse phase column (4.6×150 mm, The Separations Group, Hesperia, Calif, USA). The column is equilibrated in a mixture of 70% TFA 0.1 % in water and 30% TFA 0.08% in acetonitrile, and the product is eluted by a linear gradient over 30 min ending with a mixture of 55% TFA 0.1% in water and 45% TFA 0.08 % in acetonitrile at a flow rate of 1 ml/min. The eluate is monitored for absorbance at 216 nm and individual peaks are collected manually according to the UV absorbance. Denatured, monomeric TGF-β3 is eluted at 21.5 min. Depending on the individual reverse phase column used for the separation the same preparation of TGF-β3 is eluted around 16 min and 18 min, respectively.

TGF-β3 fractions are analysed by RP-HPLC using the same column and solvent system as above. TGF-β3 is eluted by a linear gradient over 42 min starting from 100% TFA 0.1% in water and ending with a mixture of 30% TFA in water and 70% TFA 0.08% in acetonitrile. TGF-β3 is eluted as a single peak after 30.4 min. Depending on the individual column used retention times of 29 min and 29.9 min, respectively, are obtained.

EXAMPLE 3E

Analysis of Monomeric TGF-β3 by SDS-PAGE

Individual aliquots of the Sephacryl S-100 column (Example 3.B) or the reverse phase column (Example 3.D) are dried in vacuo and analysed by SDS-PAGE on 15% polyacrylamide slab gels stained with Coomassie Blue R-250. A single band of an apparent molecular mass of about 12.000 Da is obtained which is indistinguishable from reduced natural porcine TGF-β3.

EXAMPLE 3F

N-terminal Amino Acid Sequence Determination of Monomeric TGF-β3

TGF-β3 from Example 3.B is evaporated in vacuo, dissolved in 25 µl 0.1M acetic acid and subjected to amino acid sequence determination on a gas phase protein sequencer model 470A (Applied Biosystems).

The N-terminal amino acid sequence is identical to that shown in the sequence listing under SEQ ID No. 6.

EXAMPLE 4

In Vitro Folding of TGF-β3 in Dimethylsulfoxide (DMSO) Containing Buffer

TGF-β3 obtained as described above is folded at 4° C. in a buffer consisting of 0.1M Tris, 1M NaCl, 0.5M arginine, 5 mM reduced glutathione and 40% (v/v) DMSO respectively. The pH of the buffer is adjusted to pH 9.5 with NaOH. The final concentration of TGF-β3 is 0.1 mg/ml. After 7 days at 4° C. the solution is acidified with concentrated acetic acid to pH 3.5, concentrated about 10 times by ultrafiltration in an Amicon stirred cell with YM10 membrane (Amicon). The concentrated solution is diluted to the original volume with 0.1 M acetic acid and reconcentrated. This procedure is repeated 2 times. The solution is then subjected to ion exchange chromatography as described hereinafter.

EXAMPLE 5

In Vitro Folding of TGF-β3 in Dimethylformamide (DMF) Containing Buffer

TGF-β3 obtained as described above is folded at 4° C. in a buffer consisting of 0.1M Tris, 1M NaCl, 0.5M arginine, 5 mM reduced glutathione and 30% (v/v) DMF respectively. The pH of the buffer is adjusted to pH 8.5. The final concentration of TGF-β3 is 0.1 mg/ml. After 7 days at 4° C. the solution is acidified with concentrated acetic acid to pH 3.5, concentrated about 10 times by ultrafiltration in an Amicon stirred cell with YM10 membrane (Amicon). The concentrated solution is diluted to the original volume with 0.1 M acetic acid and reconcentrated. This procedure is repeated 2 times. The solution is then subjected to ion exchange chromatography as described hereinafter.

EXAMPLE 6

Isolation of Dimeric Biologically Active TGF-β3 by Cation Exchange Chromatography The solution obtained in Example 4 or Example 5, respectively, containing between about 10 and 50 mg TGF-β3 is loaded at 6 ml/min onto a HiLoad 26/10 S-Sepharose High Performance column (Pharmacia). The column is first washed with 20 mM sodium acetate, 30% isopropyl alcohol, pH 4.0 (buffer A) for 5 minutes and then eluted with a linear gradient over 45 min starting with buffer A containing 0.2 M NaCl and ending with buffer A containing 0.5 M NaCl. The eluate is monitored at 280 nm and fractionated manually. Fractions are checked for dimeric TGF-β3 by non-reducing SDS-PAGE and for biological activity by in vitro bioassay.

EXAMPLE 7

Further Purification and Characterization of Dimeric TGF-β3

EXAMPLE 7A

Purification by RP-HPLC

Fractions containing dimeric biologically active TGF-β3 are pooled, dialysed against 0.1 M acetic acid or diluted with the same volume of 0.1% TFA in water and subjected to RP-HPLC on a Vydac 214TP510 column (1 cm×25 cm, The Separations Group, USA). The column is equilibrated at a flow rate of 4.5 ml/min with a mixture of 75% solvent A [TFA 0.1% in water] and 25% solvent B [TFA 0.08% in acetonitrile]. After loading of the sample the column is washed under equilibration conditions until the absorption monitored at 235 nm has reached baseline level. The column is then eluted within 30 min with a linear gradient starting at equilibration conditions and ending with a mixture of 45% solvent A and 55% solvent B. The eluate is fractionated manually and analyzed by non-reducing SDS-PAGE and by in vitro bioassay.

EXAMPLE 7B

Analysis by SDS-PAGE

Aliquots of the purified TGF-β3 of example 7A are dried in vacuo and analyzed by SDS-PAGE (Laemmli, U. K. (1970) Nature 227, 680) on 15% polyacrylamide slab gels stained with Coomassie Blue R-250. The unreduced sample exhibits a single band of apparent molecular mass of around 25 kDa, whereas the reduced sample shows a band at around 12.5 kDa.

EXAMPLE 7C

Molecular Mass Determination

Purified TGF-β3 from example 7A is analyzed by Electrospray Ionization Mass Spectrometry (ESI-MS). The total mass found is very close to the theoretically expected value.

EXAMPLE 7D

Amino Acid Analysis

Amino acid analysis was performed as described in Knecht, R. and Chang, J.-X., Analytical Chemistry 58:2375–2379(1986). The results are in good agreement with the theory.

EXAMPLE 7E

N-terminal Amino Acid Sequence Determination

10–20 µg of TGF-β3 of example 7A is evaporated in vacuo, dissolved in 25 µl 10 mM acetic acid and subjected to amino acid sequence determination on a gas phase sequencer model 477A (Applied Biosystems). The amino acid sequence of the first 10 residues determined was as expected from the theory.

EXAMPLE 7F

Proteolytic Fragmentation with Asp-N protease

92 μg (6.7 nmoles) TGF-β3 are reduced, 4-vinylpyridyl-ethylated, dried in an vaccum centrifuge and redissolved in 200 μl 5 mM HCl. 200 μl 0.2 M Tris-acetate buffer, pH 7.8, containing 10 mM Zwittergent 3-12 detergent (Calbiochem Corporation, La Jolla, Calif.) is added and mixed with the protein solution. The cleavage is carried out with 2 μg (dissolved in 50 μl water) endoproteinase Asp-N (from Pseudomonas fragi mutant, Sequence Grade, Boehringer Mannheim Biochemica, FRG) at 37° C. After 13 hours, 50 μl 10% (v/v) TFA are added and the mixture is separated by RP-HPLC on a Vydac 218TP5415 column (4.6 mm×150 mm, The Separations Group) with a linear gradient of 5 to 45% (v/v) acetonitrile in 0.1% TFA/water in 40 min at a flow rate of 0.1 ml/min. Isolated peptides are analyzed by Electrospray Ionisation Mass Spectrometry, ESI-MS. The molecular masses determined are in good agreement with the calculated values for the expected Asp-N fragments.

The fragments identified cover the complete amino acid sequence with the exception of residues 1 and 2. These amino acids are identified by the N-terminal sequence determination of the whole protein and by the analysis of the V8 fragments.

EXAMPLE 7G

Proteolytic Fragmentation with V8 Protease

Similarly to Example 11 with Asp-N protease 4-vinylpyridylated TGF-β3 is digested with protease V8 and the fragments separated by RP-HPLC and analysed by ESI-MS. The molecular massed determined are in good agreement with the theoretical values further proving the identity of TGF-β3. The fragments identified cover the whole sequence of 112 amino acid residues.

EXAMPLE 8

In Vitro Activity Test for Folded TGF-β: Mink Lung Epithelial Cell (Mv-1-Lu) Acid Phosphatase Assay TGF-β or hybrid protein is screened in vitro, in a cellular bioassay which measures the potency of the compound in inhibiting the growth of a continuous mink lung epithelial cell line Mv-1-Lu (ATCC/CCL64). The Mv-1-Lu cell line has proven to be a sensitive reporter in the bioassay for TGF-βs, exhibiting a sigmoid-shaped concentration response with a reported EC50 of approximately 10–50 pg/ml (Tucker et al., Science 1984; 226: 705–707; Absher et al., J Immunol Methods 1991; 138: 301–03; Danielpour et al., J Cell Physiol 1989; 138: 79–86). Mv-1-Lu cells, whose proliferation is strongly inhibited by TGF-β, is currently considered as the cell line most suitable for the development of an analytical bioassay for this cytokine (Kelley et al., Exp Lung Res 1992; 18: 877–887; Meager, J Immunol Methods 1991; 141: 1–14). The assay is performed in 96-well microtitre plates using cells which were originally obtained, at passage 46, from the American Type Culture Collection, Rockville Md., USA. The cells are seeded at low density (5000 cells per well) in growth medium (Minimum Essential Medium with 5% v/v Foetal Calf Serum) containing serial dilutions of a TGF-β standard or sample. Assays are then incubated at 37° C. in a humidified 5% $CO_2$ incubator for 72 hrs. Inhibition of cell proliferation is determined by a sensitive enzymatic cell staining method (which gives a colorimetrical estimate of the amount of acid phosphatase produced in each well), the intensity of staining corresponding to the number of cells present in each well. The absorbance O.D. of each well is determined at 405 nm and the assay data is plotted and analysed by means of a suitable PC software programme. In this assay, one Unit (U) of activity is described as the amount of TGF-β required for half-maximal inhibition of Mv-1-Lu cell proliferation.

EXAMPLE 9

In Vivo Activity Tests for Folded TGF-β3

EXAMPLE 9A

Healing of Partial-Thickness Wounds in Old Mice

It is recognised that wound healing processes become impaired with advancing age (Grove, G. L. (1982) Arch. Dermatol. Res. 272:381) and therefore represent major problems in the field of geriatric medicine. Therefore, the in vivo biological effects of the folded active dimeric TGF-β3 on the healing of partial-thickness wounds (formed by second degree burning) are investigated in a partially deficient or impaired wound repair situation, namely in old animals, using the following protocol similar to the one described by Schultz, G. S. et al. (1987) Science 235:350.

Single middermal thermal injuries are made on the dorsal thorax of anaesthetized old C57/BL6 mice (aged 450 days or more), whose backs have been previously shaved and depilitated with a commercial cream-type hair remover, by a single 10 second application of a brass template (1×1 cm, 8 gm) which has been equilibrated at 80° C. in a water bath. The resulting blister is surgically removed and the burns are treated daily, for 5 days, with a topical application of 25 μl sterile vehicle buffer solution (consisting of 0.8% w/v Hydroxypropyl cellulose in a solution of 10 mM Histidine, 140 mM NaCl, pH7.4) containing various amounts (500 ng, 100 ng or 10 ng) of the folded active dimeric TGF-β3, or with buffer solution alone, or are left untreated. All topically applied materials are sterile, endotoxin-free and pyrogen-free, and all mice are individually caged for the duration of the experiment. Each experimental group consists of 5 animals.

After 5 days of treatment with TGF-β3, the mice are anaesthetized, the blisters (if present) are surgically removed from the burns, and the burns are photographed. Areas of burns that have regenerated epithelium are outlined onto uniform thickness transparent overhead projector film and the percentage of each original burn area that has healed is calculated by planimetry. Results are also compared with the epithelial regeneration process in young (56–84day old) C57/BL6 mice with identical middermal burns which are left untreated for the duration of the experiment.

The results of the planimetrical analyses demonstrate that topical application of folded active dimeric TGF-β3 daily for 5 days in a suitable vehicle buffer stimulates and accelerates epithelial regeneration in partial-thickness wounds on old mice in a dose dependant fashion when compared with vehicle buffer only or untreated wounds. Young mice are apparently competent enough to successfully re-epithelialize their wounds in the absence of any topically applied TGF-β3. Histological analyses reveal the extent of the enhanced re-epithelialization process together with a hyperkeratosis of the regenerated epidermis on Day 6 in the TGF-β3-treated wounds.

EXAMPLE 9B

Healing of Full-Thickness Wounds in Adult Rats

The biological effects of folded active dimeric TGF-β3 are also investigated in a second in vivo model of wound repair, namely on the healing of full-thickness wounds (formed by surgical incisioning) in adult rats, using the following protocol similar to the one described by Mustoe, T. A. et al. (1987) Science 237:1333.

Single, full-thickness 5 cm long linear incisions are made with surgical scissors 1.5 cm on both sides of the dorsal midline of pentobarbitone anaesthetized male Wistar rats (300–350 g) whose backs have been previously shaved and depilitated with a commercial cream-type hair remover. In the experimental groups, edges of the left side incisions (as viewed with the dorsal side uppermost) receive single topical applications (100 μl ) of a sterile vehicle buffer (consisting of 0.8% w/v Hydroxypropyl cellulose in a solution of 10 mM Histidine, 140 mM NaCl, pH7.4) containing various amounts (2 μg, 1 μg, 0.1 μg or 0.01 μg) of a folded active dimeric TGF-β3. Edges of the contralateral right side incisions receive corresponding equal amounts of a placebo control (Bovine Serum Albumin) in the said vehicle buffer and edges of incisions in control animals receive vehicle buffer alone in the left side incisions and no treatment in the right side incisions following surgical incisioning. All topically applied materials are sterile, endotoxin-free, and pyrogen-free. Edges of each wound are then coapted with 5 evenly placed, interrupted horizontal mattress sutures of 5-0Ethilon. All animals are caged separately and the wounds are left to heal for varying periods up to and including 21 days post treatment. After sacrifice the entire dorsal skin is removed from each animal and all subcutaneous fat is carefully dissected from the underside of each of the skins using a surgical scalpel. A template consisting of two parallel surgical blades (8 mm distance between blades) is then used to excise strips of skin (between sutures on each incision) for tensile strength measurements. Samples are taken from one end of each incision for histological analysis. The maximum load tolerated by each excised skin sample is measured with a Universal Tensile Strength Machine Model 144501 (Zwick, Ulm, FRG).

Measurements are made on 30 mm×8 mm strips which are secured between hydraulic clamps and then stretched to breaking point at a rate 10 mm per minute, with the maximum load recorded on a chart recorder. Measurements are made on triplicate samples from each wound and experimental groups consisted of 4 animals. Breaking strength is not measured on wounds showing evidence of infection or excessive haemorrhaging (less than 3% of all wounds).

The results of the tensile strength measurements demonstrate that a single topical application of folded active dimeric TGF-β3 in a suitable vehicle buffer enhances the breaking strength up to 2 fold, and accelerates the healing, of full-thickness incisional wounds in adult rats in a dose dependent fashion over a 21 day time period when compared against the control group, istological analyses reveal the marked increase influx of mononuclear cells, fibroblasts and collagen production in TGF-β3-treated wounds over the 21 day period as compared to control wounds. A transient hyperkeratosis is also evident in TGF-β3-treated wounds up to 14 days after the treatment.

EXAMPLE 10

Preparation of Solubilized Monomeric Hybrid TGF-β Proteins 5 ml of plasmid pPLMu are linearized by digestion with NocI and SalI and gel purified as described above for the fragment DNAs. 100 ng of the linearized and purified pPLMu vector DNA and 3×the molar equivalent of the respective purified fragment DNA coding for hybrid TGF-β1-3, TGF-β2-3 and TGF-β3-2, respectively, shown in the sequence listing are incubated at 4 C. for 15 h in 20 ml ligation buffer (70 mM TRIS-HCl, pH7.5, 10 mM MgCl2, 5 mM DTT, 0.1 mM Adenosine-triphosphate) containing 1 unit of DNA ligase (Boehringer). 10 ml of the ligation mixture are added to 200 ml of cold (4 C.) competent E.coli LC137 cells carrying plasmid pcI857. After 30 min the cells are heat shocked by incubation for 1.5 min in a 42 C. water bath. 2 ml of LB medium are added and the culture is shaken for 60 min at 30 C. 200 ml aliquots are plated on LB plates containing Ampicillin and Kanamycin and incubated for 22 h at 30° C. Single colonies are cultivated and plasmid DNA is analysed. Subcloning of the DNA fragments coding for TGF-β1 -3, TGF-β2-3 and TGF-β3-2 in pPLMu results in plasmids pPLMu.TGF-β1 (44/45)β3, pPLMu.TGF-β2(44/45)β3 and pPLMu.TGF-β3(44/45)β2 respectively. Clones containing the above constructs are referred to as E.coli LC137/pPLMu.TGF-β1 (44/45)β3, E.coliLC137/pPL-Mu.TGF-β2(44/45)β3 and E.coli LC137/pPLMu.TGF-β3 (44/45)β2, respectively.

E.coli LC137/pPLMu.TGF-β1 (44/45)β3, E.coliLC137/pPLMu.TGF-β2(44/45) β3 and E.coli LC137/pPLMu.TGF-β3(44/45)β2 are heat induced as follows (see also example 3.A) and the expressed proteins are analysed by SDS-PAGE. TGF-β1-3, TGF-β2-3 and TGF-β3-2 all appear as heat induced proteins 2 h after heat induction migrating with an apparent molecular mass of approximately 12.000 Da Overnight cultures of E.coli LC 137/pPLMu.TGF-β1 (44/45)β3, E.coli LC 137/pPLMu.TGF-β2 (44/45)β3 and E.coli LC137/pPLMu.TGF-β3(44/45)β2 in 2 l Erlenmeyer flasks containing 750 ml of LB medium with 40 mg/l of Ampicillin and Kanamycin are grown at 30 C. 300 ml of the overnight cultures are added to 750 ml of LB medium containing antibiotics as mentioned above in 2 l Erlenmeyer flasks and heated to 42 C. by shaking for approximately 3.5 min in a 65 C. water bath. The flasks are then transferred to a 42 C shaker and incubated for 3 h. The flasks are cooled down to 12 C. in an ice water bath and the cells are collected after centrifugation for 10 min at 8.000 rpm in a GSA rotor (Sorvall).

The procedures given below for the production of the monomeric solubilized TGF-β1 -3 hybrid are also applied to for the solubilization of TGF-β2-3 and TGF-β3-2.

E.coli LC137/pPLMu.TGF-β1 (44/45)β3 cells are fermented as described above and inclusion bodies are prepared as follows. Cell disruption and recovery of the inclusion bodies is performed at 4 C. About 18 g of wet cells are suspended in 60 ml of 0.1 M TRIS/HCl, 10 mM EDTA, 1 mM PMSF (Phenyl Methan Sulphonyl Fluoride), pH 8.3 (disruption buffer). The cells are passed two times through a Frenchpress (SLM Instruments, Inc.) according to the manufacturers instructions and the volume is brought to 200 ml with the disruption buffer. The suspension is centrifuged for 20 min at 15.000 g. The pellet obtained is suspended in 100 ml disruption buffer containing 1 M NaCl and centrifuged for 10 min as above. The pellet is suspended in 100 ml disruption buffer containing 1% Triton X-100 (Pierce) and again centrifuged for 10 min as above. 0.3 g of the washed pellet is then suspended in 10 ml of 20 mM Tris/HCl, 1 mM EDTA, 1 mM PMSF, 0.1% DTT, pH 8.0, and stirred with a magnetic stirrer for 1 h at room temperature. The sample is then brought to pH 2.5 with concentrated acetic acid and homogenised in a Teflon tissue homogenizer and centrifuged in a Centricon H-401 centrifuge (Kontron Instruments) with a fixed angle rotor A.8.24 for 60 min, at 15 C. and 12 000 rpm. The acetic acid of the clear supernatant is exchanged with 10 mM HCl in an Amicon 8010 stirred cell with YM05 filter by repeated concentration and dilution of the solution with 10 mM HCl.

EXAMPLE 11

Series of Refolding Experiments with Different TGF-βs and TGF-β-Hybrids

The versality and broad applicability of the invention is exemplified by the results summarized in the following series of examples. The specific conditions and the individual proteins used in the in vitro protein refolding experiments are listed. Other experimental conditions are as described in Example 4. Biological activity was determined 3 and 7 days after the start of in vitro protein folding.

In vitro Folding in Organic Solvent without Detergent: Results of Bioassay

| No | RSH | DMSO | DMF | pH | TGF-β | Activity |
|---|---|---|---|---|---|---|
| 1.) | 2.5 mM GSH | 10% | | 9.5 | β3 | + |
| 2.) | 2.5 mM GSH | 20% | | 9.5 | β3 | + |
| 3.) | 2.5 mM GSH | 30% | | 8.0 | β3 | + |
| 4.) | 2.5 mM GSH | 30% | | 9.5 | β3 | ++ |
| 5.) | 2.5 mM GSH | 40% | | 9.5 | β3 | ++ |
| 6.) | 2.5 mM GSH | 50% | | 9.5 | β3 | ++ |
| 7.) | 2.5 mM GSH | 40% | | 6.5 | β3 | + |
| 8.) | 2.5 mM GSH | 40% | | 7.5 | β3 | + |
| 9.) | 2.5 mM GSH | 40% | | 8.5 | β3 | + |
| 10.) | 2.5 mM GSH | 40% | | 10.5 | β3 | ++ |
| 11.) | 0.0 mM GSH | 40% | | 9.5 | β3 | + |
| 12.) | 2.5 mM GSH | 40% | | 9.5 | β3 | + |
| 13.) | 2.5 mM GSH | 40% | | 9.5 | β1-3 | + |
| 14.) | 2.5 mM GSH | 40% | | 9.5 | β3-2 | + |
| 15.) | 2.5 mM GSH | 40% | | 9.5 | β2-3 | + |

In vitro Folding in Organic Solvent without Detergent: Results of Bioassay

| No | RSH | DMSO | DMF | pH | TGF-β | Activity |
|---|---|---|---|---|---|---|
| 16.) | 2.5 mM GSH | | 10% | 9.5 | β3 | + |
| 17.) | 2.5 mM GSH | | 20% | 9.5 | β3 | ++ |
| 18.) | 2.5 mM GSH | | 30% | 9.5 | β3 | ++ |
| 19.) | 2.5 mM GSH | | 40% | 9.5 | β3 | + |
| 20.) | 2.5 mM Cysteine | 40% | | 9.5 | β3 | + |
| 21.) | 2.5 mM Cysteamine | | 40% | 9.5 | β3 | + |

RSH: sulfhydryl reagent as specified in the table
GSH: reduced glutathione
DMSO: dimethylsulfoxide
DMF: dimethlyformamide
β3: TGF-β3
β2: TGF-β2
β1-3: TGF-β1-3 Hybrid
β3-2: TGF-β3-2 Hybrid
β2-3: TGF-β2-3 Hybrid
Activity:
+: medium activity in the in vitro bioassay described in example 8
++: high activity in the in vitro bioassay described in example 8

Deposition of Microorganisms

The following microorganisms were deposited at the Deutsche Sammlung von Mikroorganismen (DSM), Mascheroder Weg 1b, D-3300 Braunschweig (FRG):

| microorganism | deposition date | accession number |
|---|---|---|
| E. coli LC 137/pPLMu.hTGF-β1 | Nov. 28, 1989 | DSM 5656 |
| E. coli LC 137/pPLMu.hTGF-β2 | Nov. 28, 1989 | DSM 5657 |
| E. coli LC 137/pPLMu.hTGF-β3 | Nov. 28, 1989 | DSM 5658 |
| Saccharomyces cerevisiae GRF18 | Mar. 4, 1986 | DSM 3665 |

The invention claimed is:

1. A process for the production of a dimeric, biologically active Transforming Growth Factor type β2 (TGF-β2) or β3 (TGF-β3), or a salt thereof, comprising the step of treating the denatured monomeric form of said TGF-β2 or β3 with a folding buffer, wherein said folding buffer consists of glutathione in its reduced form and an organic solvent which is DMSO (Dimethylsufoxide) or DMF (Dimethylformamide) or a mixture of DMSO and DMF; thereby permitting folding of the monomeric TGF-β2 or β3 into the spatial conformation which is associated with the biological activity, while retaining said monomer in a soluble form.

2. The process according to claim 1 in which DMSO is used at a concentration of about 30% to about 50% (vol/vol).

3. The process according to claim 1 in which DMF is used at a concentration of 40% (vol/vol).

4. The process according to claim 1 wherein the organic solvent is a mixture of DMSO and DMF and the mixture is used in a concentration of 10% to about 50% (vol/vol).

5. The process according to claim 1 in which the buffer has a pH of about 8.5 to about 10.

6. The process according to claim 1 in which the buffer has a temperature of about 0° C to about 40° C.

7. The process according to claim 1 in which the reduced glutathione is used in a concentration of about 1 mM to 100 mM.

* * * * *

UNITED STATES PATENT AND TRADEMARK OFFICE
CERTIFICATE OF CORRECTION

| | | |
|---|---|---|
| PATENT NO. | : 7,057,016 B2 | Page 1 of 1 |
| APPLICATION NO. | : 09/813271 | |
| DATED | : June 6, 2006 | |
| INVENTOR(S) | : Nico Cerletti | |

It is certified that error appears in the above-identified patent and that said Letters Patent is hereby corrected as shown below:

On the title page

Item (63) should read:

Related U.S. Application Data

(63) Continuation of application No. 09/316,724, filed on May 21, 1999, now abandoned, which is a continuation of application No. 08/776,444 (now abandoned) filed as application No. PCT/EP95/02719 on July 12, 1995.

Column 1,

The first paragraph under the title should read:

Item [63]
-- This is a continuation of U.S. application Ser. No. 09/316,724, filed on May 21, 1999, now abandoned, which is a continuation of U.S. application Ser. No. 08/776,444, filed on Juanuary 24, 1997, now abandoned, which is a 371 of PCT/EP95/02719, filed on July 12, 1995. --.

Signed and Sealed this

Sixteenth Day of January, 2007

JON W. DUDAS
*Director of the United States Patent and Trademark Office*